(12) United States Patent
Haj-Yehia

(10) Patent No.: US 6,900,338 B1
(45) Date of Patent: May 31, 2005

(54) SCAVENGER COMPOUNDS

(75) Inventor: Abdullah Haj-Yehia, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/856,616

(22) PCT Filed: Nov. 25, 1999

(86) PCT No.: PCT/IL99/00638

§ 371 (c)(1),
(2), (4) Date: Jul. 31, 2001

(87) PCT Pub. No.: WO00/31060

PCT Pub. Date: Jun. 2, 2000

Related U.S. Application Data
(60) Provisional application No. 60/110,037, filed on Nov. 25, 1998.

(51) Int. Cl.[7] .................. C07D 339/00; C07D 409/00; C07D 411/00; A61K 31/385; A61K 31/40
(52) U.S. Cl. .............. 549/20; 549/22; 549/35; 549/39; 549/59; 548/527; 514/440; 514/436; 514/433; 514/444; 514/422
(58) Field of Search ................ 514/440, 436, 514/433, 444, 422; 549/20, 22, 35, 39, 59; 548/527

(56) References Cited

U.S. PATENT DOCUMENTS

| | | | |
|---|---|---|---|
| 4,808,480 A | | 2/1989 | Regen |
| 5,334,612 A | * | 8/1994 | Kalden et al. .............. 514/440 |
| 6,204,288 B1 | * | 3/2001 | Pershadsingh et al. ...... 514/440 |
| 6,251,935 B1 | * | 6/2001 | Schoenen et al. ........... 514/440 |
| 6,313,164 B1 | * | 11/2001 | Fujita et al. ................. 514/440 |
| 6,331,559 B1 | * | 12/2001 | Bingham et al. ........... 514/440 |
| 6,369,098 B1 | * | 4/2002 | Pershadsingh et al. ...... 514/440 |
| 6,387,945 B2 | * | 5/2002 | Packer et al. ............... 514/440 |

FOREIGN PATENT DOCUMENTS

| | | |
|---|---|---|
| DE | 44 17 038 | 11/1995 |
| EP | 0 869 126 | 7/1998 |
| WO | WO 98 42661 | 10/1998 |

OTHER PUBLICATIONS

A.F Wagner: "Properties and Derivatives of alfa–LIPOIC ACID" Journal of the American Chemical Society vol. 78, 1956, pp. 5079–5081 XP002129541 Americal Chemical Society, Washington, DE., US ISSN: 0002–7863 p. 5081, col. 2, paragraph 4.

* cited by examiner

Primary Examiner—Deborah C. Lambkin
(74) Attorney, Agent, or Firm—Eitan, Pearl, Latzer & Cohen Zedek, LLP

(57) ABSTRACT

The present invention provides novel compounds having scavenging and anti-ROS properties and pharmaceutical composition comprising these compounds for treatment of conditions associated with oxidative stress or free radical injury. The compounds of the invention are of general formula (I).

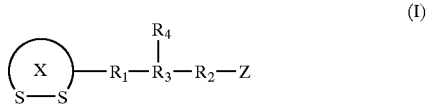

9 Claims, 5 Drawing Sheets

SCAVENGER COMPOUNDS

CROSS-REFERENCE TO RELATED APPLICATIONS

This application is a National Phase Application of PCT International Application No. PTC/IL99/00638, International Filing Date Nov. 25, 1999, claiming priority of U.S. Provisional Patent Applications, 60/110,037, filed Nov. 25, 1998.

FIELD OF THE INVENTION

The present invention relates to molecules capable of acting as scavengers of free radicals, metals and reactive oxygen species, to a method for their preparation and to pharmaceutical compositions containing then.

BACKGROUND OF THE INVENTION

An intense interest in the relationship between oxidative stress and diseases has characterized the last two decades since the observation that oxidative modification of low-density lipoprotein (LDL) leads to foam cell formation and atherosclerosis. Convincing evidence exists that, by opposing the reactive oxygen species (ROS) mediated processes (i.e., lipid peroxidation and other direct hazardous effects) in the body, anti-reactive oxygen-species (Anti-ROS)-antioxidant compounds exert beneficial effects in atherosclerosis and other pathologies involving oxidative stress and free radical injury.

The term "oxidative stress" is commonly used in reference to biological systems as a means to characterize the total burden of potentially harmful reactive oxygen species that are present in tissues as a consequence of routine cellular oxidative metabolism of both endogenous and exogenous compounds. The term itself is a misnomer because many of the chemical reactions that contribute to oxidative-stress are not oxidative in nature. For example, although it usually fictions as a reducing agents the production of superoxide anion in biological systems is often described as a type of oxidative stress. To initiate lipid peroxidation, superoxide must first be converted to another radical species such as the hydroxyl radical via dismutation to hydrogen peroxide, followed by reduction of hydrogen peroxide to hydroxyl radical via the Fenton reaction. [1]. Others may define oxidative stress as the production of free radical species in vivo, though, a number of species associated with oxidative stress either are not radicals or radical species that are not inherently deleterious.

Endothelial cell smooth muscle cells, and monocytes all produce superoxide anion and other ROS under physiological conditions.

The recent discovery of the central role played by the endothelium-derived relaxing factor (EDRF), in control of blood flow and fluidity through the generation of biochemical species that inhibit platelet activation and deposition, prevent thrombus formation, and limit inappropriate vasoconstriction. initiated a series of studies defining the cardinal impact of reactive oxygen species on the activity of EDRF.

EDRF identified as NO or a closely related redox form of NO (i.e., S-nitrosothiol), acts to dilate vascular smooth muscle and inhibit platelet adhesion by activating guanylyl cyclase (GC) and increasing intracellular cyclic-3',5'-guanosine monophosphate (cGMP) [2,3]. EDRF is constitutively produced and also released from endothelial cells via receptor-mediated mechanisms after exposure to a number of clinically relevant agonists [4]. In addition to EDRF, the vascular endothelium produces a number of vasoactive substrates [5] which act in concert with EDRF to mediate endothelial control of vascular tone and platelet and monocyte activity.

The mechanisms by which superoxide and other ROS may contribute to abnormalities in EDRF action are diverse. Superoxide may react destructively with NO and limit the biological activity of EDRF [6]. Superoxide production may lead to formation of hydroxyl radicals which may be cytotoxic to endothelial cells [7] through direct peroxidation of lipids and proteins. Hydrogen peroxide is formed during the dismutation of superoxide and may, in addition to peroxynitrite, also oxidize available free and proteinous thiol groups that may be important for EDRF action. Hydrogen peroxide is a principal mediator of neutrophile-induced injury to endothelial cells and its effects on other physiological functions are complex, although oxidation of intracellular thiols is a likely mechanism for these effects because pretreatment with dithiothreitol prevents $H_2O_2$ mediated cell dysfunction. Hydroxyl radicals have been implicated in tissue damage resulting from repelfusion injury and inflammation, and may be present in athereosclerotic lesions [8]. Organic peroxyl radicals have been implicated in a wide variety of biochemical processes, and these species combine readily with NO leading to the formation of peroxynitrite.

In addition to inactivation of EDRF, oxidative depletion of vital thiol groups may be the mechanism through which ROS exert cell toxicity and dysfunction.

Ample evidence exists that links biological thiols to EDRF action and metabolism. NO is a reactive molecule that readily combines with a number of biochemical species producing a variety of derivative oxides of nitrogen. These derivatives are themselves reactive and can form adducts with readily available sulfhydryl species under physiological conditions producing stable, biologically active S-nitrosothiols that possess biochemical, vasorelaxant and platelet inhibitory properties both in vitro and in vivo [9, 10]. Because S-nitrosothiols possess properties reminiscent of EDRF, many have speculated that EDRF may be a nitrosothiol rather than authentic NO [3].

Thiol availability in mediating the effects of endogenous NO and of exogenous NO-donors (i.e., organic nitrates) is of critical importance [24]. It was demonstrated that the redox-sensitive extra/intracellular thiol content may have critical implications, not only for EDRF (NO) action and metabolism, but also regarding the mechanisms by which anti-ROS thiol-containing compounds may prove useful in preserving normal cellular function as well as preventing/reversing pathological conditions involving NO, thiols and ROS.

The body is endowed against the deleterious effects of ROS, with a number of antioxidant defense mechanisms, which may be divided into three major groups. The first group, enzymatic antioxidants, represents the main form of intracellular antioxidant defenses and mainly includes SOD, catalase, and glutathione peroxidase. The second group, nonenzymatic protein antioxidants, is primarily found in plasma and is mainly represented by GSH, and some proteins such as transferrin albumin, and ceruloplasmin, which also has enzymatic (ferroxidase) activity. Finally, the non-enzymatic low molecular weight antioxidants are found in plasma, extracellular and intracelluar fluids, lipoproteins, and cell membranes. This group of antioxidants may be further subdivided into water-soluble (i.e., GSH, uric and ascorbic acids, and bilirubin) and lipid-soluble antioxidants which are localized to cell membranes and to lipoproteins and include α-tocopherol, β-carotene, and ubiquinol 10. Other endogenous low molecular weight species present in plasma and extracellular fluids also have antioxidant properties including phenolic estrogens, thyroxin and catecholamines.

A possible mechanism of antioxidant-mediated preservation of cellular function is decreased oxidative modification of LDL. However, recent evidence suggests that both water- and lipid-soluble antioxidants may have important physiological effects that are not directly related to the protection of LDL-against oxidation in vivo. Although these alternative effects of antioxidants may not bear directly on EDRF action, they have the potential to influence processes that are known to impair redox-dependent enzymatic and non-enzymatic metabolic processes. One may also speculate that the antioxidant activity of agents like vitamin E and β-carotene, may reflect the free-radical-scavenging characteristics of these agents vis-a-vis superoxide anion or hydroxyl radicals, either directly or via modulation of enzymes action. However, because they lack the possibility to exist in an equilibrium between die two possible forms [disulfide (oxidized) <-> thiols (reduced)] when overdosed, vitamin E, as well as most other currently available antioxidants may adversely affect the course of the disease for which they are indicated [12].

Thiols are more central to cellular antioxidant defense mechanisms than any other existing antioxidant present in the cell (i.e. endothelium, brain, skin and other tissues). However, thiol antioxidants that are effective in vitro, may not be effective in vivo. For example, the thiol antioxidant GSH would seem an ideal candidate for treating endothelial dysfunction and many other diseases involving oxidative stress. Unfortunately, GSH is not absorbed from the diet or through the skin. N-Acetylcysteine (NAC), which provides cysteine for GSH synthesis, and which is readily absorbed and transported is an alternative. However, side effects including nausea vomiting, and diarrhea greatly limit its clinical effectiveness for enteral administration and its extreme instability limits its topical administration [13].

Thus, very few successful pharmacological intervention strategies are currently available for the treatment of endothelial dysfunction and other pathologies involving oxidative stress and free radical injury. Vitamin E, vitamin C, probucol and β-carotene constitute most of antioxidants currently applied. Unfortunately, however, none of these agents by itself (or when combined with others) can adequately address cellular (i.e., skin or endothelial) dysfunction and other oxidative stress-mediated pathologies. Because of their 'mode' of action, tissue uptake and other relevant characteristics, all currently available antioxidants can (if at all!) only indirectly affect EDRF metabolism and action act only on certain ROS, and adversely affect the course of the disease if incorrectly dosed.

Lipoic acid (LA), is frequently referred to as "a universal antioxidant" [14]. LA, as lipoamide, has long been known for its role in oxidative metabolism as an essential cofactor in mitochondrial -keto acid dehydrogenase complexes, which was previously thought to be its only role LA is readily taken up by a variety of cells and tissues and is rapidly reduced to their sulfhydryl (dithiol)-form (the dihydroform), as both in vitro and in vivo [15,16]. The reducing power for this comes from both NADH and NADPH [17].

Numerous studies have demonstrated that both LA and DHLA are antioxidants [18,20]. LA scavenges hydroxyl radicals, hypochlorous acid, peroxyl radicals, and singlet oxygen. It also chelates iron, copper, and other transition metals. In addition to those species (including transition metals) acted upon by LA, DHLA scavenges superoxide radicals and peroxyl radicals For example, LA has been shown to modulate cellular reducing equivalent and thus favorably affect complications of diabetes and ischemic injury [17]. LA was also shown to protect against ROS-mediated brain damage following cerebral ischemia in various animal models [21]. It protects against aminoglycoside-induced nephrotoxicity [22]. Both LA and DHLA were shown to protect against peroxynitrite-dependent tyrosine nitration and alpha I-antiproteinase inactivation [23]. In the working heart model of ischemia-reperfusion, LA (especially the R-enantiomer) has been shown to enhance the aortic flow during reoxygenation [24]. In addition, because of its bioconversion to DHLA, administration of LA has been shown to also regenerate other endogamous antioxidants. Current evidence indicates that DHLA can reduce GSSG to GSH, dehydroascorbate and semidehydroascorbyl radical, and ubiquitione, all of which can contribute to vitamin E regeneration from its oxidized form, as well as to reduce thioredoxin [25].

Studies employing diverse types of thiols have been carried out both in vivo and in vitro. None of the studies involving thiols have ever evaluated the role of the dithiol α-lipoic acid (LA, thioctic acid, 1,2-dithiolane-3-valeric acid, 6,8dithiooctanoic acid) or analogs thereof in EDRF or NO-donors action as well as in other pathologies including senescence-mediated wrinkle formation of skin in general, and of facial skin in particular.

SUMMARY OF THE INVENTION

It is all object of the present invention to provide compounds having scavenging and anti-ROS properties, which overcome the limitations of the currently available scavenger and antioxidant molecules.

The compounds of the present invention are of the general formula I:

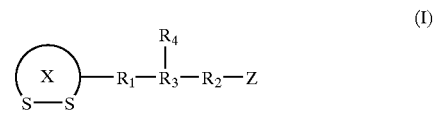

in which

X denotes a 4–10 membered ring;

$R_1$ and $R_2$ are independently alkyl or alkylene;

$R_3$ denotes H, carboxy, amido, amino, carboxyalcohol, alkanediol, amine alcohol, amino diol, thio or amine carbonyl;

$R_4$ denotes H or 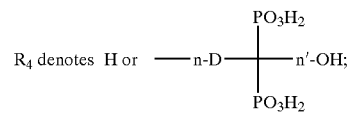

n and n' are, independently, an integer from 0 to 8;

D denotes $CH_2$ or NH;

Z denotes a 4–10 membered di sulfide ring or $R_4$, and its salts.

Preferably X denotes a 4, 5 or 6 membered ring and Z denotes a 4, 5 or 6 membered di sulfide ring or $R_4$.

Preferably $R_1$ and $R_2$ are $C_{1-10}$ alkyls or alkylenes.

$R_1$ or $R_2$ or both may be substituted by substituents selected from the group consisting of halogen atoms, halomethyl groups, oxo, hydroxy, carboxy, carboxyalkyl, alkoxy, alkoyl, alkyloxy, aryloxy, aryloxyl and aryloyloxy, amino, alkylamino, dialkylamino, cyano, azido and nitro, thiol, alkylthiol, sulphonyl, sulphoxide, thienyl, furanyl, pyrrolyl, imidazolyl, pyrazolyl, thiazolyl, isothiazolyl, oxazolyl, pyrrolidinyl, pyrrolinyl, inlidazolidinyl, imidazolinyl, pyrazolidinyl, tetrahydrofuranyl, pyranyl, pyronyl, pyridyl, pyrazinyl, pyridazinyl, benzofuranyl, isobenzofuryl, indolyl, oxyindolyl, isoindolyl, indazolyl, indolinyl, 7-azaindolyl, isoindazolyl, benzopyranyl, coumarinyl, isocournarinyl, quinolyl, isoquinolyl, naphthridinyl, cinnolinyl, quinazolinyl, pyridopyridyl, benzoxazinyl, quinoxadinyl, chromenyl, chromanyl, isochromanyl, carbolinyl, substituted or unsubstituted alkyl groups, and substituted or unsubstituted aryl groups.

The present invention further relates to a method for the preparation of a compound of general formula I comprising the step of performing reduction or oxidation of a compound of the general formula II

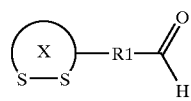

and a compound of the general formula III

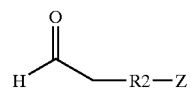

in the presence of a reducing or oxidizing agent and a solvent. The present invention further relates to a method for treating a patient afflicted with conditions associated with oxidative stress or fee radical injury comprising the step of administering to the patient an effective amount of the compound of general formula I.

BRIEF DESCRIPTION OF THE FIGURES

The present invention will be understood and appreciated more fully from the following detailed description taken in conjunction with the appended figures in which.

DETAILED DESCRIPTION OF THE INVENTION

Figure 1:
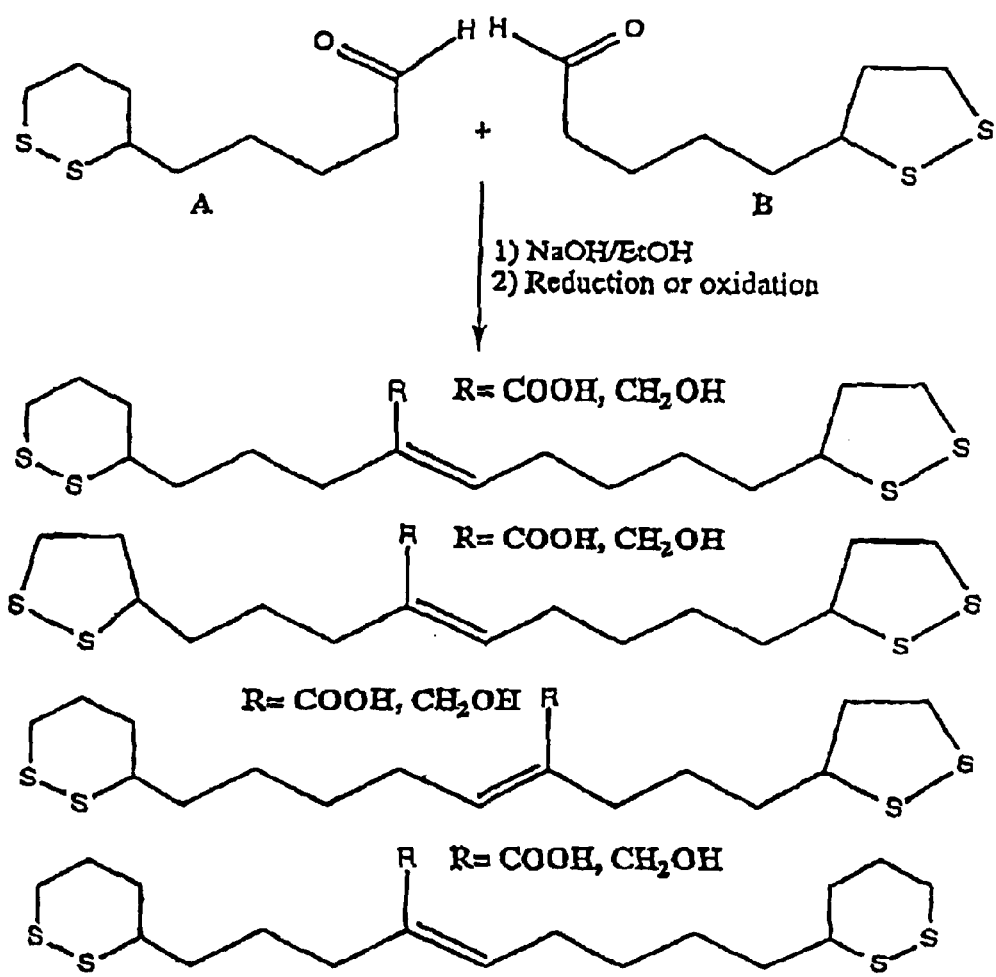
FIG. 1 illustrates the synthetic scheme according to an embodiment of the invention.

The compounds of the present invention are scavenger compounds which are LA analogs designed according to the rational which will now be discussed in detail.

Nitrate tolerance may be regarded as a "special form of thiol depletion" and the ability of the compounds of the invention to increase cellular GSH and the availability of other reducing equivalents, may prove useful in preventing nitrate tolerance, as evident from the results with lipoyl lipoate which, when co-administered with conventional nitrates, currently in clinical use, prevents/retards tolerance development.

The remarkable ability of the interconversion of disulfide <-> dihydro to affect cellular reducing homeostasis via modulation of NADH/NAD+ and NADPH/NADP+ratios and other routes demonstrates how intimately the compounds of the invention can be connected to cell metabolism and redox states.

In contrast to GSH, the compounds of the invention are readily absorbed from the diet and through the skin transported, taken up by cells and reduced to the dihydro form in various tissues, including the endothelial lining and the smooth muscle cell components of blood vessels (see results). The sulfhydryl (dithiol) thus formed is also exported from cells and can provide antioxidant protection to extracellular compartment and nearby cells. Thus, like LA, the proposed compounds seem especially promising as an antioxidant for the treatment of pathologies involving oxidative stress and free radical injury.

Because of these characteristics and the very low toxicity expected from these LA analogs, they may, like LA itself, be successfully used as therapeutic agents in human clinical trials for the treatment of conditions such as diabetes, ischemia-reperfusion injury, heavy metal poisoning, radiation damage, neurodegenerative disorders, mitochondrial cytopathies and HIV infection [18,20].

Ample evidence exists to support the excessive vascular ROS production in atherosclerosis, hypercholesterolemia, hypertension and diabetes mellitus. Each one of these diseases is now regarded as a part of a syndrome rather than a distinct disease and, in concert, they constitute the "deadly quartet", referred to as 'Reaven's Syndrome'or Syndrome-X. Recently, it has been shown that gentamicin-induced nephropathy also involves superoxide and other ROS. Convincing evidence also exists to support the primary involvement of ROS in the abnormal action of NO that characterizes the endothelial dysfunction accompanying these diseases. Because of their metal (radical) scavenging and anti-ROS properties, the compounds of the invention may exert beneficial effects on the natural course and outcome of these diseases as well as of other pathologies. Considering their promising chemical and pharmacological characteristics, as is so far evident from the results, and the ever increasing demand for better therapy for these diseases, significant potential exists for these compounds to become prototype anti-oxidative stress-mediated cellular dysfunction agents. This is especially true considering recent evidence indicating the involvement of NO. ROS and thiols in a variety of conditions, the pathogenesis of which as well as the treatment for, have not been fully resolved. These include (but are not limited to): aging and aging-mediated changes (including those involving appearance and skin), pulmonary and ocular hypertension, asthma and other related respiratory diseases, trauma, neurotoxicity, neurological and neurodegenerative disorders [i.e. stroke, Huntington, Alzheimer and Parkinson's diseases, multiple sclerosis and convulsive (seizure) disorders], AIDS-related disorders (i.e., dementia), disorders of gastric acid and other secretary and peristaltic functions of the alimentary system, inflammatory bowel diseases (Crohn's disease and ulcerative colitis), drug and disease-induced neuropathy and nephropathy, pathological and premature uterine contractions, chemotactic, phagocytic and other cellular defense impairment in immunological disorders, aggregation disorders, pregnancy-induced hypertension, cerebrovascular diseases, penile erection and treatment of male impotence [4–7.17–20]. In all of these pathologies, evidence also exists to support the favorable effects of various anti oxidants.

However, none of the currently available antioxidants addresses oxidative stress mediated cellular dysfunction by favorably affecting the major species involved in the process, that is, by protecting against all types of ROS, favorably affecting cellular reducing equivalents either directly or via regeneration and recycling of other major endogenous antioxidants, and yet, being a sulfhydryl donor, is expected to favorably affect NO action. In fact, the results show that co-administration of compound 2 (see FIG. 2) with classical NO-donors can significantly retard the development of tolerance to their effect. Thus, our belief in the dependency of the integrity of endothelium and other cellular functions on the relative concentrations of NO. ROS and thiols, as well as in the deleterious effects of cellular dysfunction on basic physiological functions, brought us to design and synthesize these compounds. Because of (heir promising chemical and biological activity characteristics demonstrated by the results, significant potential exists for compounds of this type to serve both as protectors against tolerance development to nitrovasodilators, and, because of their anti-ROS activity, as promising disease-modifying agents of pathologies involving oxidative stress and free radical injury.

The rationale for the design of these compounds is further supported by die following:
1. Agents possessing antioxidant or SOD-like activity have been shown to as potentiate nitric oxide-mediated relaxation, both in vitro and in vivo.
2. As is the case for LA (I), it is expected that the following alcohol (II), anilide (III) and ester (M derivatives will be chemically stable, cell-permeable, and potentially non-toxic compounds that will possess similar anti-ROS activity (see results).

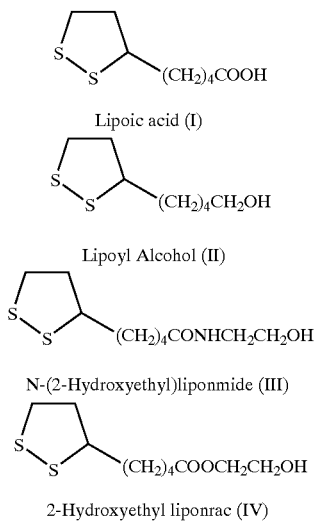

Lipoic acid (I)

Lipoyl Alcohol (II)

N-(2-Hydroxyethyl)liponmide (III)

2-Hydroxyethyl liponrac (IV)

3. When LA is administered concomitantly with NO donors, it enhances its activity and retards tolerance development, both in vitro and in vivo (see results).
4. In fact, LA was shown to possess beneficial effects in diseases involving endothelial dysfunction by its own [17–20], and an inclusion of lipoyl-like ester or lipoyl-like ester as in the chemical structures of the invention is expected to form a novel anti-ROS-compounds, as the results show.

Thus, according to the present invention, there are provided chemical compounds comprising one or more disulfide moieties (or their dihydro forms if stable) contained in a ring form The compounds of the present invention provide cytoprotective effect probably by acting as an antioxidant scavenger of reactive oxygen species, including; superoxide anion, hydroxyl radicals, peroxynitrite, peroxyl radicals, hypochlorous acid, hydrogen peroxide and transition metals (especially copper and ferrous) and give rise to both a direct benefit derived from removal of injurious ROS and an indirect benefit by protecting both ambient and endogenous and liberated erogenous NO from inactivation by these ROS.

The compounds of the invention may be employed in the treatment of any condition associated with oxidative stress or free radical injury like endothelial dysfunction, aging (including senescence-associated changes in skin and appearance) and diseases like diabetes mellitus, cardiovascular diseases (such as ischaemic heart disease, angina pectoris, myocardial infraction, congestive heart failure, atherosclerosis, hypertension and arrhythmia), asthma, trauma, shock (hypovolumic, neurogenic or septic), neurotoxicity, neurodegenerative and neurological disorders (including Alzheimer and Parkinson's diseases, amyotrophic lateral sclerosis, multiple sclerosis, convulsive (seizure) disorders, AIDS-dementia and disorders which involve processes of teaming and memory), disorders of gastric secretions, relaxation and peristalsis of the intestinal tract (including inflammatory bowel diseases), drug and disease-induced nephropathies, pathological (premature) and physiological uterine contractions, cellular defense impairment, endothelial dysfunction-induced diseases and insulin-resistance in diabetes, pregnancy-induced hypertension, chemotaxis and phagocytic impairment in immunological disorders, cerebrovascular diseases, aggregation disorders, fertility and reproductive disorders (erg, penile erection and treatment of male impotence).

Compounds of the present invention may be administered in a form suitable for oral use, for example a tablet, capsule, aqueous or oily solution, suspension or emulsion; for topical we including transmucosal and transdermal use, for example a cream, ointment, gel, aqueous or oil solution or suspension, salve, parch or plaster, for nasal use, for an example a snuff nasal spray or nasal drops; for vaginal or rectal use, for example a suppository; for administration by inhalation, for example a finely divided powder or a liquid aerosol; for sub-lingual or buccal use, for example a tablet or capsule, or for parenteral use (including intravenous, subcutaneous, intramuscular, intravascular or infusion), for example a sterile aqueous or oil solution or suspension. In general the above compositions may be prepared in a conventional manner using convention excipients, using standard techniques waft known to those skilled in the art of pharmacy. Preferably, the, compound is administered orally.

For oral administration, the compounds of the invention will generally be provided in the form of tablets or capsules, or as an aqueous solution or suspension.

Tablets for oral use may include the active ingredient mixed with pharmaceutically acceptable excipients such as it diluents, disintegrating agents, binding agents, lubricating rents, sweetening agents, flavoring agents, colouring agents and preservatives. Suitable inert diluents include sodium and calcium carbonate, sodium and calcium phospha and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Capsules for oral use include hard gelatin capsules in which the active ingredient is mixed with a solid diluent, and soft gelatin capsules wherein the active ingredient is mixed with water or an oil such as peanut oil, liquid parafin or olive oil. For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

It will be appreciated that the invention is described by way of example only, and that modifications of detail may be made without departing from the scope of the present invention.

EXPERIMENTAL
Synthesis of Compounds

The following are only representative procedures for synthesis of selected compounds. The compounds for which the method of perpetration is described below were purposefully selected as to represent the general approach used to prepare compound from all figures depicting the structures suggested by the present invention.

Figure 2:
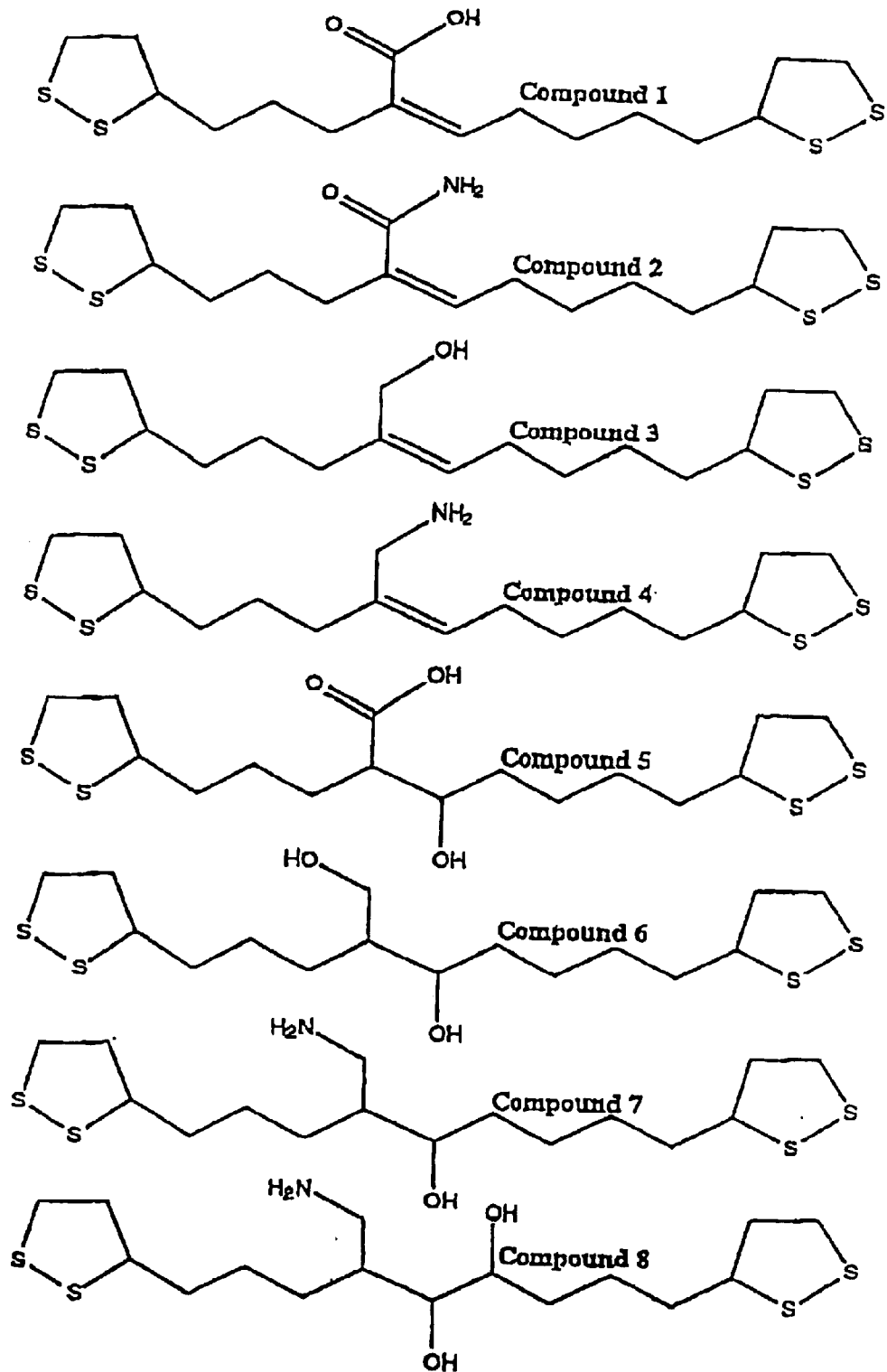
FIG. 2 illustrates compounds containing two five atom rings according to an embodiment of the invention.

To synthesize compounds like those depicted in FIG. 2 the acid analog has to fist be converted to che active aldehyde form (A or B type compounds shown in FIG. 1). The aldehyde was usually prepared by mild oxidation of the corresponding alcohol. Using lipoic acid as an example, the following describes a general method for preparation of the alcoholic precursors.

Alcohol preparation

The acid (0.25 M) is dissolved under nitrogen atmosphere in 250 ml of dry (freshly distilled) tetrahydrofuran (THF) and cooled to −5" on ice-salt bah. To this, a cold borane-THF solution (Aldrich) is added dropwise with vigorous stirring until TLC analysis shows comply conversion of the acid to the alcohol (only a slight excess of borane is usually needed). Upon completion, 50 ml of cold methanol is added to the reaction mixture to destroy excess of borane and the organic solvent removed under reduced pressure. The crude alcohol (usually in more than 95% yield) is immediately used for the preparation of the aldehyde.

Aldehyde preparation

The alcohol (0.25 M) is dissolved in 250 ml of dichlorometane containing 0.5 mole of p-toluene sulfonic acid (or camphoric sulfonic acid) and the resulting solution is cooled on an ice bath. To this is added dropwise a cold solution of 0.5 M N-acetyl-TEMPOL(Aldrich) dissolved in 250 ml of dichlorometane during 30 ml. Upon completion of the addition, the mixture is stirred for an ational 1 hr in the cold and then at root temperature for 3–7 hours (or until all alcohol has disappeared by TLC). The solution is filtered and the organic solvent is washed twice with 5% sodium bicarbonate ons solution, twice with 5% hydrochloric acid solution and solvent removed under reduced pressure. A portion of the residue is chromatographed on silica gel using a hexane-dichloromethane (1:1) mixture for analytical characterization and the remaining portion is used for the condensation without further purification. For Michael type condensation, the same aldehyde or combined with different aldehyde is dissolved in ethanol and cooled on an ice bath. Cold 30% of ethnolic potassium hydroxide solution is added dropwise and the mixture stirred overnight under nitrogen atmosphere. Depending on the structure of the aldehyde, TLC analysis usually reveals the completion of the condensation reaction within 12–24 hours. An equal volume of water is added and the reaction mixture is extracted three times with ether. The ether extracts (containing ethanol) is dried over sodium sulfate and evaporated to dryness. The residue is applied onto a silica gel column (200 g) and eluted with a chloroform:hexane:ethyl acetate mixture (2:1:1). The resulting aldehyde (or mixture of aldehydes) was recovered in varying good to excellent yields.

Compound 1:

Lipolal (0.5 M) is dissolved in 100 ml of dry ethanol and the mixture cooled on an ice bath. 10 ml of cold 59% ethanolic sodium hydroxide solution is added over 10 minutes and the mixture stirred under nitrogen atmosphere overnight. The reaction is quenched with 100 ml of cold water and extracted twice with 150 ml of diethyl ether. The organic layer is separated and dried for an hour over anhydrous sodium sulfate and evaporated to dryness. The residue is applied onto a silica gel column (100 g) and eluted as described above. The pure aldehyde is recovered in 81% yield. A portion (0.1 M) of the aldehyde is dissolved in 50 ml of THF and added dropwise to a cold 0.2 M suspension of argentum oxide freshly prepared from the addition of argentum nitrate to 100 ml 0.1 M sodium hydroxide solution. The reaction is stirred on an ice bath for 3 hrs during which the conversion of the aldehyde to the acid is monitored by TLC analysis. Upon completion, the reaction mixture is neutralized with concentrated hydrochloric acid and immediately extracted with two portions each of 150 ml of diethyl ether. The ether layer is separated and dried over anhydrous sodium sulfate and evaporated to dryness. The solid residue can usually be crystallized from a mixture of ethanol water to furnish a high (>90%) yield of pure compound 1.

Compound 2:

Compound 1 (0.05 M) is dissolved in 50 ml of dry dichloromethane and added to a cold solution of 0.06 M of DCC in 50 ml of dichloromethane. The reaction is stirred for half an hour on an ice bath. N-Hydroxy succinimide (0.075) is added and the reaction stirred overnight under nitrogen. The reaction mixture is filtered and the precipitate washed twice with 30 ml of cold dichloromethane. The organic layer is evaporated to half its original volume, hilt again and added dropwise to 100 ml of 1 M cold solution of ammonia in methanol (Aldrich). The reaction is stirred for 1.5 hours upon which the organic, solvent is evaporated to dryness. The solid residue is recrystallized from dioxane to furnish 87% of pure compound 2.

Compound 3:

The condensation product of lipolal (0.05 M) is separated on silica column as described above. The pure aldehyde is dissolved in 150 ml of dry THF and cooled on an ice bath A cold 1 M borane-THF solution is added dropwise under nitrogen and the reaction monitored by TLC analysis until the aldehyde is completely reduced (usually a slight excess of borane is used). The reaction is immediately quenched with cold methanol and evaporated to dryness under reduced pressure. The viscous residue (more then 95% pure) is further purified by application onto silica gel column and eluted with ethyl acetate:chloroform (1:3) mixture. The eluate is evaporated under reduced pressure to furnish a 76% yield of pure compound 3.

Compound 4:

Compound 3 (0.06 M) in 50 ml of dichloromethane is added dropwise to a solution of triphenyl phosphine (0.1 M) containing 0.15 M of zinc bromide and a catalytic amount of 1,1'-azobis(cyclohexanecarbonitrile). The reaction is stirred for 8 hours or until TLC analysis shows the complete conversion of the alcohol into the bromide derivative. The reaction mixture is filtered and the filtrate wash with dichloromethane. The filtrate is mixed with an equal volume of n-hexane and filtered again. The filtrate is then evaporated to dryness. The resulting crude bromide is then extracted by trituration with hexane. The combined hexane triturates awe evaporated to dryness and the residue applied onto a silical gel column and eluted with dichloromethane:hexane (1:1) mixture. The organic solvent is evaporated to dryness under reduced pressure and the residue dissolved in chloroform (50 ml) and added in one portion to an excess solution of ammonia in chloroform. The reaction is stirred for 10 hours at room temperature upon which it is filtered. The filtrate is evaporated to dryness and the residue dissolved in 15 ml of chloroform and applied on aluminum oxide column. The amine is eluted with chloroform:ethyl acetate: triethyl amine (1:1:0.01) mixture. Evaporation of the solvent furnished 82% yield of pure compound 4.

Compound 9:

Lipolal (0.05 M) and 6,9-dithiane nonanal (0.05 M) are dissolved in cold 100 ml of ethanol containing 3 g of potassium hydroxide. The reaction is monitored by TLC and processed for separation of the four possible products (see synthetic scheme 1) by chromatography as described above to furnish, after, oxidation with silver oxide, an almost equal amounts of compound 9, compound 1, and compound 17.

Compound 10:

Compound 10 is synthesized from compound 9 by a similar procedure as for compound 2.

Compound 11:

Compound 11 is synthesized from the aldehyde precursor of compound 9 as described for compound 3.

Compound 12:

Compound 12 is synthesized from the alcohol precursor, via the bromide intermediate, as described for compound 4.

Compound 17:

This compound is obtained as one of the separation products of the reaction mixture as described for the synthesis of compound 9.

Compound 18:

This compound is obtained from compound 17 via a similar procedure used for the preparation of compound 2.

Compound 19:

This compound was obtained from the reduction of the aldehyde precursor of compound 17 as described for compound 3.

Compound 20:

This compound is prepared from the alcohol precursor, via the bromide derivative, as described for compound 4.

Figure 4:
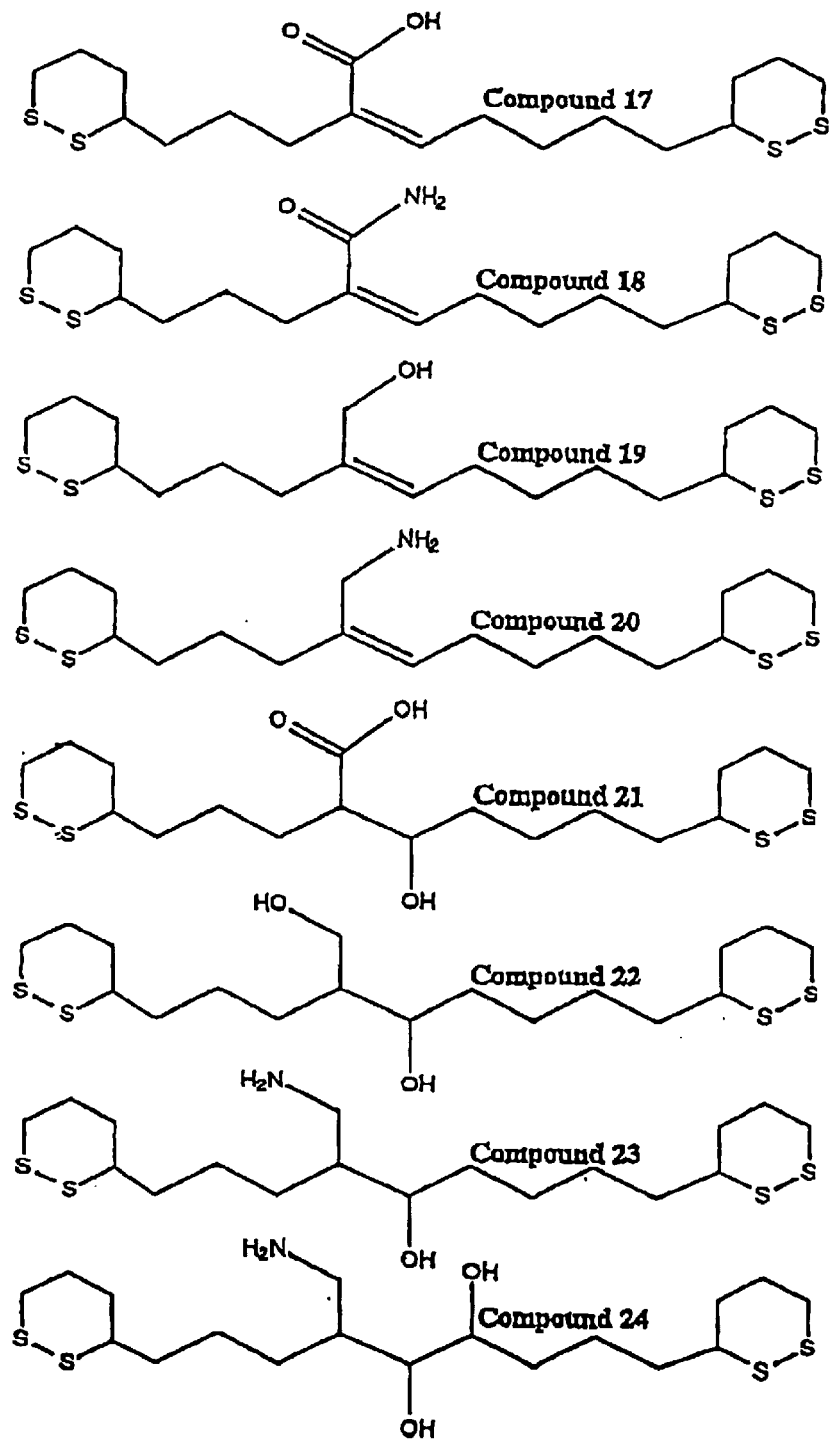
FIG. 4 illustrates compounds containing two six atom rings according to an embodiment of the invention.
Figure 5:
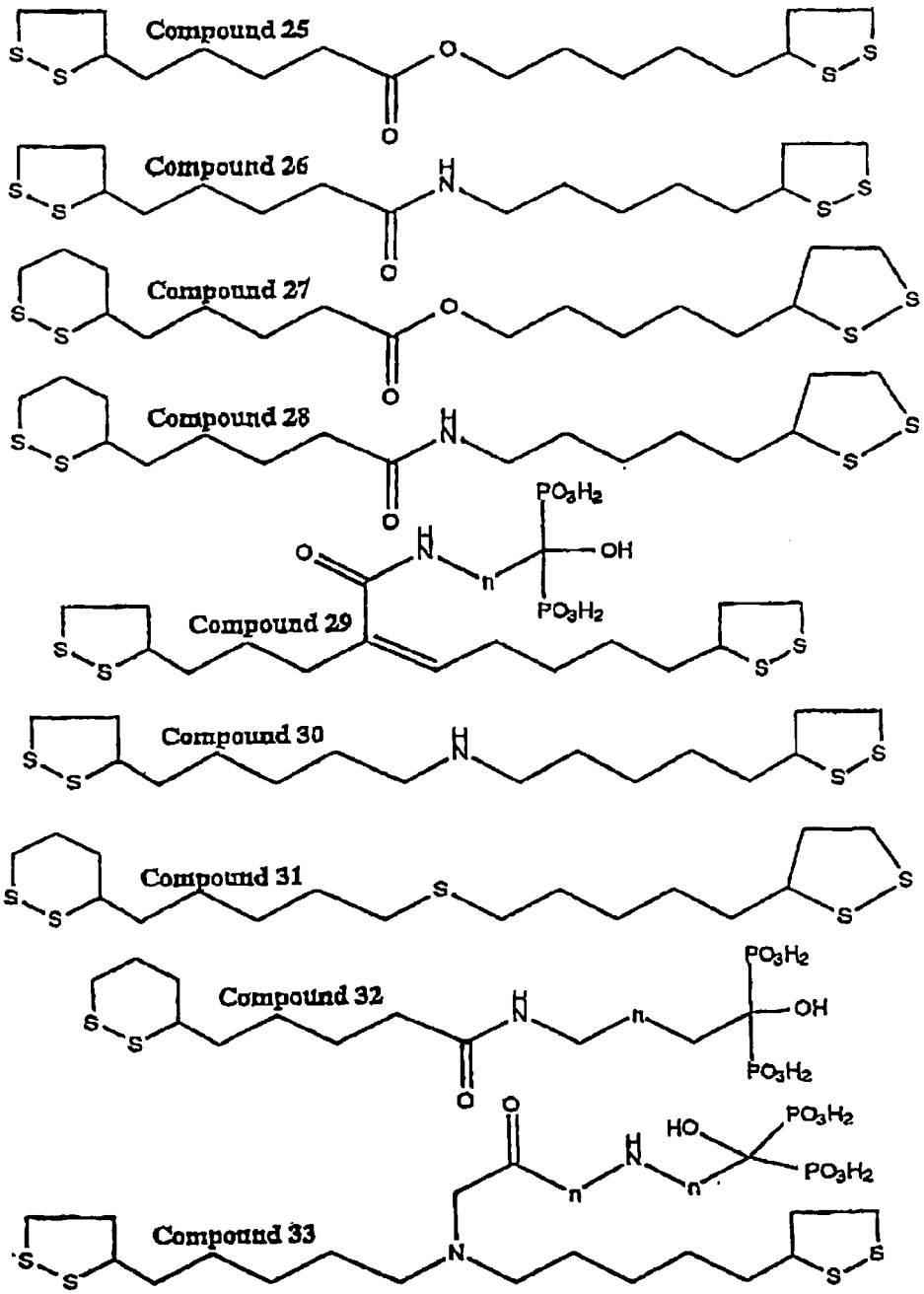
FIG. 5 illustrates compounds composed of the alcohol, amide and ester, ether, sulfide, phosphate and diamine from the same or different nucleus, according to an embodiment of the invention.

Compound 25:

Compounds of the type depicted in FIG. 4 are easily synthesized by the usual methods of ester and amide preparation. For example, compound 25 is easily synthesized by refluxing for 3–5 hours of equimolar amounts of lipoic acid and lipolol in benzene in the presence of a catalytic amount of concentrated sulfuric acid. The benzene is washed twice with aqueous 10% potassium carbonate solution and evaporated to compound 25 in 95% yield.

This type of compound is easily synthesized by addition of lipoamine to dichlorometane solution of N-hydroxy succinimide activated ester of lipoic acid. Upon stirring for 1 hour in the cold and overnight at room temperature, the reaction mixture is successively washed with water, 5% potassium carbonate solution, 5% hydrochloric acid solution and saturated sodium chloride, dried on anhydrous magnesium sulfate and evaporated to dryness. This usually furnishes the product in a pure form, or, depending on the purity of the reactants, may necessitate the purification by chromatography to furnish pure compound 26.

Compounds 27 and 28:

The ester (compound 27) and the amide (compound 28) are prepared in a similar way as compounds 25 and 26, respectively.

Compounds 29, 32, and 33:

These compounds are easily prepared by reacting the activated ester of the acid with the appropriate amino alkyl phosphonate derivative. The resulting products ae purified by chromatography to fish the title compound in a fair to good yield.

Compound 30 and 31:

The dilipoyl amine is synthesized by reacting excess lipoamine with lipoyl bromide, whereas compound 31 is obtained by reacting the bromide derivatives of the precursors with sodium in acetonitrile or DMF.

Results

I. Prevention of nitrate tolerance:

a) Acute effects: Rats (Spargue-Dawely) weighing 300–400 g were treated with an intravenous (i.v.) bolus dose of 2 mg nitroglycerin (NTG) before and after pre-treatment with the compounds (50 mg/kg) administered intraperitoneally. Compounds 1 and 2 from FIG. 1, compounds 9 and 10 from FIG. 2, compounds 17 and 18 from FIG. 3, compounds 25 a nd 26 from FIG. 4 were dissolved in a mixture of ethanol:propylene glycol:water (1:1:1) and administered in 1 ml intraperitoneally one hour before NTG administration. One minute after the NTG administration, the rats were sacrificed by decapitation and the aorta was removed quickly, immersed in a phosphate buffer solution containing 20 mM EDTA and immediately frozen in liquid nitrogen add stored at −70° until analyzed. Next day, the tissue were analyzed for their cGMP content. After thawing, tissue were weighed and homogenized in EDTA-phosphate buffer, centrifuged and the super collected into another tube. The pellet was washed with 1 ml buffer, vortex-mixed, centrifuged and the supernatant added to the second tube. 2 ml of acetonitrile were added to the tube containing the combined extracts and the tube vortex-mixed, centrifuged and the supernatant collected to another clean tube. The aqueous-acetonitrile solution in this latter tube was evaporated to dryness and the reside dissolved in assay buffer. The cGMP content of the solution was determined using a radioimmunoassay (RIA-Amersham) as previously reported by us [26,27].

The following describes representative cGMP values from aorta treated only with NTG or with NTG a pretreatment with the compounds (given for compound 1):

|  | NTG alone | NTG + Compound 1 |
| --- | --- | --- |
| cGMP (pmol/g tissue) | 175 ± 13 | 216 ± 21* |

*Significantly different from NTG alone (p < 0.005).

Thus, compound 1 significantly increases issue guanylyl oyolase response to nitrates. Similar significant increases were also obtained when pre-treatment was performed with other compounds (see above).

b) Prevention: Rat were administered a continuos infusion of NTG known to induce tolerance [26,27] with or without concomitant administration of the compounds (the same tested for the acute effects). The compounds were administered either in continuos i.v. infusion or intraperitoneally in 4 separated doses (q 6 hours). The effects on vascular (aortic) guanylyl cyclase activity was then evaluated as described above for control rats.

|  | NTG-pretreatment | NTG + Compound 1 |
|---|---|---|
| cGMP (pmol/g tissue) | 64 ± 9* | 183 ± 14** |

*Significantly different from NTG alone treatment of control rats and denotes tolerance to NTG effect.
**Not significantly different from NTG alone in control rats and denotes the lack of tolerance development to NTG effects on vascular cGMP.

Thus, pretreatment with compound 1 prevents tolerance development to NTG Similar results were obtained with other compounds were tested.

II. Protection against streptozotocin-induced diabetes

Rats (Sprague-Dawely) weighing 200–350 g were treated by a singe i.v. dose of streptozotocin (STZ, 50 mg/kg) through the tail vein to induce diabetes. Rats were monitored for weight, glucose levels, and plasma lipids. Below are some of the preliminary results obtained in control rats, streptozotocin-diabetic, rats and rats started on a treatment with compound 1 immediately upon streptozotocin administration.

|  | Con. rats | STZ-pretreated | STZ + Com. 1 |
|---|---|---|---|
| Weight (grams) | 223 ± 34 | 176 ± 23* | 206 ± 27** |
| Glucose (mg %) | 131 ± 14 | 314 ± 36* | 179 ± 29** |
| Lipids (mg %) | 185 ± 19 | 319 ± 31* | 226 ± 29** |

These results clearly demonstrate the protective effects of compound 1 on complication of streptozotocin induced diabetes. This is especially true since these are known to involve oxidative stress and the radical injury and thus demonstrate the beneficial antioxidant-free radical effects of the compounds suggested by this application.

III. Protective effects against colitis

Rats (Sprague-Dawely) weighing 300–400 g were administered a single dose of 5 ml of 5% acetic (AA) solution through a rectal tube into the distal colon. The effect of acetic acid administration on the development of colitis was monitored both by visualization and by determination of mediators known to reflect oxidative stress and free radical injury. These include: 1) Myeloperoxidase activity (MPO) expressed in the following table in O.D/mg units. 2) Lipid peroxidation (LP) expressed in the following table TBARS units as nmol/mg protein of colonic tissue. 3) Protein Carbonyl content (PCC) expressed in the following table in nmol/mg protein. All three parameters are reflective of the extent of tissue oxidative stress and free radical injury.

|  | Control rats | AA-treated rats | AA + Compound 1 |
|---|---|---|---|
| PCC | 0.23 ± 0.01 | 1.5 ± 0.03* | 0.75 ± 0.02*$ |
| LP | 0.05 ± 0.01 | 0.7 ± 0.04* | 0.07 ± 0.02*$ |
| MPO | 0.0004 ± 5% | 0.02 ± 18% | 0.00075 ± 10% |

These results clearly demonstrate the beneficial effective antioxidative-anti-free radical mediated injury of compound 1 in the acetic acid model of colitis. Similar results were also obtained for other compounds as detailed.

IV. Dermatological effects

These effects were evaluated in human (male and female) volunteers who suffered from either a condition of melasma or papules on the back skin with no infective etiology. Additionally, the effects of compounds 1 and 25 were studied in female volunteers subjectively suffering from enhanced wrinkle formation on the facial skin. Here, the beneficial effects of both compounds were assessed by the volunteer himself/herself, by, a third party unaware of the treatment and objectively by the investigator who follows up those volunteers. The results so far obtained clearly demonstrate the superiority of both compounds on any other currently available formula indicate for these skin conditions. The compounds were administered in 2% emulgel or 2.5% aqueous cream preparations. No significant difference between these two vehicles was observed nor does an increase in the percentage of the active ingredient found to affect the final results.

Figure 3:
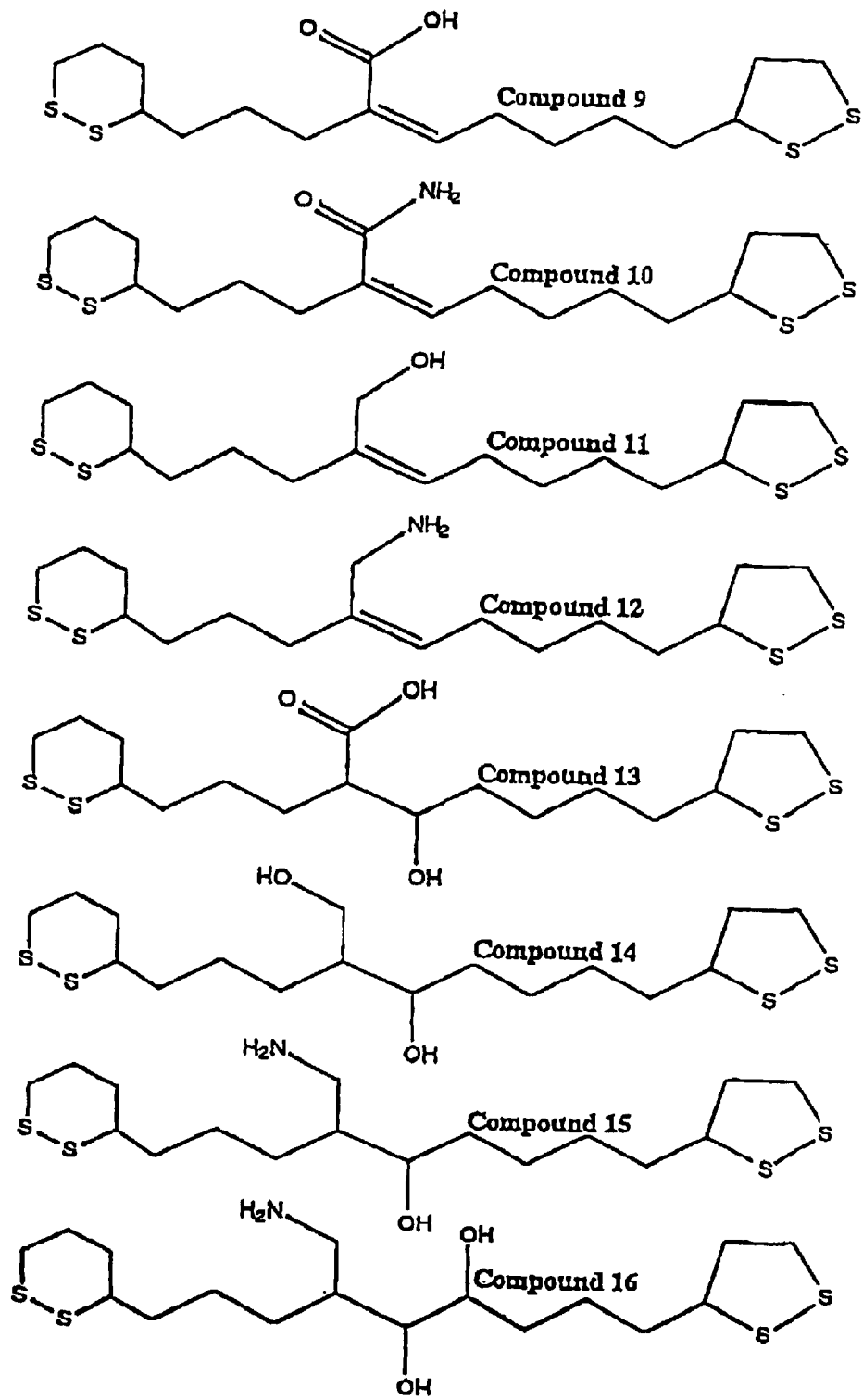
FIG. 3 illustrates compounds containing a five atom ring and a six atom ring according to an embodiment of the invention.

It will be appreciated by persons skilled in the art that the present invention is not limited by what has been particularly shown and described herein above. For example. It should be understood, that FIGS. 2–5 contain representative, examples reflecting the concept of the present invention. For example, the compounds depicted in FIG. 2 are obtained from the condensation of 2 molecules of the same structure (symmetric condensation), whereas those in FIG. 3 are obtained from the condensation of 2 different compounds. Thus, it is obvious that condensation can give rise to a mixture of compounds in which the zings are switched and the condensation can take place from either side, as shown in FIG. 1. That is, when compounds A and B are condensed, four condensation products are possible of which only representative products are shown in figure 3.

Rather the scope of the invention is defined by the claims which follow:

REFERENCES

1. Goldstein S, Meyerstein D, Czapski G: The Fenton reagents. Free Radio Biol Med 15:435–455, 1993.
2. Iguarro L. J., Buga G. M. Wood K. S.: Endothelium-derived relaxing factor produced and released from artery and vein is nitric oxide. Proc Natl Acad Sci USA 8 4:9265–6269, 1987.
3. Myers P. R., Minor R. L. Guorra R. Jr, et al: Vasorelaxant properties of endothelium-derived relaxing factor more closely resemble S-nitrosocysteine than nitric oxide, Nature 345:161–163, 1990.
4. Furchgort R: Role of endothelium in responses of vascular smooth muscle. Circ Res 35:551–573, 1983.
5. Cohen R. A.: The role of nitric oxide and other endothelium-derived vasoactive substances in vascular disease. Progress in Cardiaovasc Dis 38:105–128, 1995.
6. Gryglewski R. J., Palmer R. M. Moncada S: Superoxide anion is involved in the breakdown of endothelium-derived vascular relaxing factor. Nature 320:454–456, 1986.
7. Beckman J. S. Beckman T. W. Chen J, et. al: Apparent hydroxyl radical production by peroxynitrite: implication for endothelial injury from nitric oxide and superoxide. Proc Natl Acad Sci USA 87:1620–1624, 1990.
8. Smith C. Mitchinson M. J., Atuoma O. I., et al: Stimulation of lipid peroxidation and hydroxyl radical generation by the contents of human atherosclerotic lesions. Biochem J 286:901–905, 1992.
9. Simon D. I., Stamler J. S., Jaraki O, et al: Antiplatelet properties of protein S-nitrosothiols derived from nitric

What is claimed is:

1. A scavenger compound of the general formula I

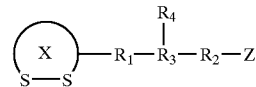

wherein

X is a 4–10 membered ring;

$R_1$ and $R_2$ are independently of each other an alkylene or alkenylene wherein said $R_1$, $R_2$ or both may be unsubstituted or substituted by substituents selected from the group consisting of pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, pyridyl, pyrazinyl, pyridazinyl, indolyl, oxyindolyl, isoindolyl, indazolyl, indolinyl, 7-azaindolyl, isoindazolyl, quinolyl, isoquinolyl, naphthridinyl, cinnolinyl, quinazolinyl, pyridopyridyl, benzoxazinyl, quinoxadinyl, and carbolinyl;

$R_3$ is carboxy, amido, alkanol, amino, carboxyalcohol, alkanediol, amine alcohol, amine dial, thio or amine carbonyl;

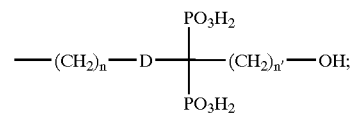

$R_4$ is null, H or n and n' are, independently, an integer from 0 to 8;

D is $CH_2$ or NH; and

Z is a 4–10 membered di sulfide ring or $R_4$ and its salts.

2. A compound according to claim 1 wherein X is a 4, 5 or 6 membered ring and Z is a 4, 5 or 6 membered di sulfide ring or $R_4$.

3. A compound according to claim 1 wherein $R_1$ and $R_2$ are a $C_{1-10}$ alkylene or alkenylene.

4. A method for the preparation of a compound according to claim 1 comprising the step of performing reduction or oxidation of a compound of the general formula II

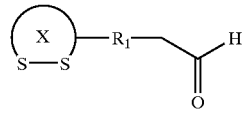

and a compound of the general formula III

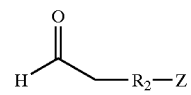

in the presence of a reducing or oxidizing agent and a solvent.

5. A method of treating a patient afflicted with conditions associated with oxidative stress or free radical injury comprising the step of administering to the patient an effective amount of the compound according to claim 1.

6. A method according to claim 5 wherein with conditions associated with oxidative stress or free radical injury are selected from aging-mediated changes, pulmonary and ocular hypertension, asthma and other related respiratory diseases, trauma, neurotoxicity, neurological and neurodegenerative disorders, AIDS-related disorders, disorders of gastric acid and other secretary and peristaltic functions of the alimentary system, inflammatory bowel diseases (Crohn's disease and ulcerative colitis), drug and disease-induced neuropathy and nephropathy, pathological and premature uterine contractions, chemotactic, phagocytic and other cellular defense impairment in immunological disorders, aggregation disorders, pregnancy-induced hypertension, cerebrovascular diseases, and male impotence.

7. A method according to claim 5 wherein the compound is administered orally.

8. A pharmaceutical composition comprising the compound according to claim 1 together with a pharmaceutically acceptable excipient.

9. A scavenger compound of the general formula

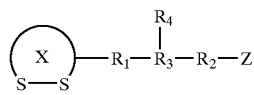

(I)

wherein

X is a 4–10 membered ring;

$R_1$ and $R_2$ are independently of each other an alkylene or alkenylene wherein said $R_1$, $R_2$ or both may be unsubstituted or substituted by substituents selected from the group consisting of pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, pyridyl, pyrazinyl, pyridazinyl, indolyl, oxyindolyl, isoindolyl, indazolyl, indolinyl, 7-azaindolyl, isoindazolyl, quinolyl, isoquinolyl, naphthridinyl, cinnolinyl, quinazolinyl, pyridopyridyl, benzoxazinyl, quinoxadinyl, and carbolinyl;

$R_3$ is alkanol, amino, carboxyalcohol, alkanediol, amine alcohol, amine diol, thio or amine carbonyl;

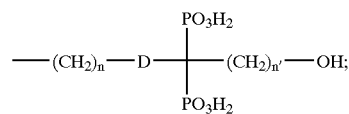

$R_4$ is null, H or n and n' are, independently, an integer from 0 to 8;

D is $CH_2$ or NH; and

Z is a 4–10 membered di sulfide ring or $R_4$ and its salts.

* * * * *